United States Patent [19]

Bowen et al.

[11] Patent Number: 4,977,325
[45] Date of Patent: Dec. 11, 1990

[54] OPTICAL READ SYSTEM AND IMMUNOASSAY METHOD

[75] Inventors: Mark S. Bowen, Medford; Stephen D. Fantone, Lynnfield; Bruce E. Miller, Brighton; Duane T. Thompson, Franklin, all of Mass.

[73] Assignee: P B Diagnostic Systems, Inc., Westwood, Mass.

[21] Appl. No.: 378,647

[22] Filed: Jul. 12, 1989

[51] Int. Cl.[5] ............................................. G01N 21/64
[52] U.S. Cl. ............................... 250/461.2; 250/372; 250/373; 250/461.1
[58] Field of Search ................... 250/461.2, 461.1, 373, 250/372

[56] References Cited

U.S. PATENT DOCUMENTS

| | | | |
|---|---|---|---|
| 3,811,777 | 5/1974 | Chance | 356/73 |
| 3,833,304 | 9/1974 | Liston | 356/414 |
| 3,963,351 | 6/1976 | Chance et al. | 356/317 |
| 3,973,129 | 8/1976 | Blumberg et al. | 250/461.2 |
| 4,031,399 | 6/1977 | Klein et al. | 250/461.2 |
| 4,133,873 | 1/1979 | Noller | 436/518 |
| 4,295,199 | 10/1981 | Curry et al. | 364/555 |
| 4,516,856 | 5/1985 | Popelka | 356/368 |
| 4,587,428 | 5/1986 | Binder | 250/372 |
| 4,795,613 | 1/1989 | Azuma et al. | 422/64 |

FOREIGN PATENT DOCUMENTS 0212455 3/1987 European Pat. Off. ......... 250/461.2

Primary Examiner—Constantine Hannaher
Attorney, Agent, or Firm—Francis J. Caufield

[57] ABSTRACT

A low cost optical system which incorporates a low ultraviolet output tungsten halogen light source and solid state photodetectors and circuitry in such a way as to provide reliable fluorometric test results. The attainment of reliable results using such components is made possible by incorporating highly ultraviolet transmissive optics to maximize ultraviolet light throughput and by using solid state circuitry together with a filter wheel having both light blocking and light passing regions in a manner which fully accounts for noise and dark signals associated with solid state photodetectors.

15 Claims, 5 Drawing Sheets

OPTICAL READ SYSTEM AND IMMUNOASSAY METHOD

BACKGROUND OF THE INVENTION

This invention relates to fluorometers and, more particularly, it concerns a low-cost and yet highly effective optical system for a dual channel, ultraviolet-visible, fluorometer in an immunoassay instrument and an associated method of fluorescence spectroscopy.

Fluorometers have gained wide acceptance for clinical analysis of blood and other biological fluids. Conventionally, fluorometers employ an optical system to subject a fluid sample, or a sample containing a fluorescent dye or tag material, to light energy at a first wavelength and cause emission of fluorescent light at a longer wavelength from the sample. The intensity of fluorescent emission is indicative of the presence or quantity of a substance in the sample under investigation. Because the amount of light absorbed and emitted by such biological fluid samples is low, conventional fluorometers are equipped with either one or both of a high output ultraviolet light source and a photomultiplier tube in order to achieve reliable test results.

High output ultraviolet light sources such as xenon arc lamps or lasers are not only expensive, but also suffer from drawbacks such as producing excessive heat, causing irreversible damage to specimens, creating noise, bleaching fluorescent tag materials, and requiring complex and expensive control systems. While it is known in the art to use a less expensive, relatively low ultraviolet output, broadband light source, such as a tungsten halogen lamp, and filter the lamp output with an ultraviolet transmitting bandpass filter, the resulting filtered radiation is of such a low level that the fluorescent light emitted by the sample is difficult to detect Heretofore, the difficulty of fluorescent light detection has been addressed exclusively by the use of an extremely sensitive photomultiplier tube to detect the low levels of sample emitted fluorescence. While providing for radiation detection even at the photon counting level, photomultiplier tubes are expensive and fragile and necessitate relatively complex control circuitry In light of the foregoing, there is a need for an improved optical fluorometer system which provides the desired analysis without requiring the use of high ultraviolet output light sources and photomultipliers. cl SUMMARY OF THE INVENTION In accordance with the present invention, an optical system for a fluorometer is provided by which reliable dual channel fluoroanalysis is effected using low cost components.

In a preferred embodiment of the present invention, a low cost and yet highly effective dual channel fluorometer, having excitation and emission branches, incorporates a relatively low ultraviolet output, tungsten halogen excitation source together with solid state photodetectors to detect the low levels of sample emitted light encountered in fluoroanalysis. The attainment of reliable results with such components is made possible by incorporating optics in the excitation and emission branches that are approximately 90 percent transmissive in the ultraviolet region to maximize throughput and by using solid state circuitry together with a filter wheel having both light blocking and light passing regions in a manner which fully accounts for dark signals associated with the solid state photodetectors and amplifiers.

In the practice of the present invention, a sample holder or assay element containing a biological fluid such as blood serum is placed above a read port of the present optical system, illumination provided by the tungsten halogen source and filtered through an excitation branch bandpass filter is focused on the front surface of the sample holder so as to cause the particular constituent under study, or a fluorescent dye or tag material in the sample, to fluoresce. The emitted fluorescence is collected and directed through an emission branch bandpass filter and focused on a photodetector. The present optical system also includes a reference photodetector for receiving illumination from the tungsten halogen source and providing a signal which is used to compensate for variations in source output.

The excitation and emission bandpass filters are carried on a filter wheel as a diametrically opposed matched pair of filters. The filter wheel also includes a pair of diametrically opposed opaque surfaces With the filter wheel in one position, the excitation and emission filters of a matched pair of bandpass filters are simultaneously placed along the excitation and emission paths of the system. With the filter wheel in another position, both the excitation and emission branches are simultaneously blocked by the opaque regions for purposes of obtaining photodetector/amplifier dark signals, which indicate component drift.

The output signals from each of the main and reference photodetectors are amplified, converted, digitized, and processed by solid state circuitry to produce a measurement which is indicative of the concentration of the agent under investigation. The processing is accomplished by using an algorithm based on four sequential photodetector signals, namely, a reference photodetector dark signal, a reference photodetector excitation signal, a main photodetector emission signal, and a main photodetector dark signal. The measurement provided by this algorithm is treated differently by the microprocessor based on the particular type of assay element being used.

A principal object of the invention, therefore, is the provision of a low-cost and yet reliable optical system for a multi-channel fluorometer. Another object of the present invention is the provision of such an optical system which is particularly suited for use in an immunoassay instrument. Yet still another object of the present invention is the use of solid state photodetectors and circuitry in a manner which compensates for the noise and dark signals inherent in such photodetector/amplifiers. Other objects and further scope of applicability of the present invention will become apparent from the detailed description to follow, taken in conjunction with the accompanying drawings in which like parts are designated by like reference characters.

BRIEF DESCRIPTION OF THE DRAWINGS

The novel features that are considered characteristic of the present invention are set forth with particularity herein, both as to their organization and method of operation, together with other objects and advantages thereof, and will be best understood from the following description of the illustrated embodiments when read in connection with the accompanying drawings wherein.

DETAILED DESCRIPTION OF THE PREFERRED EMBODIMENT

Figure 1:
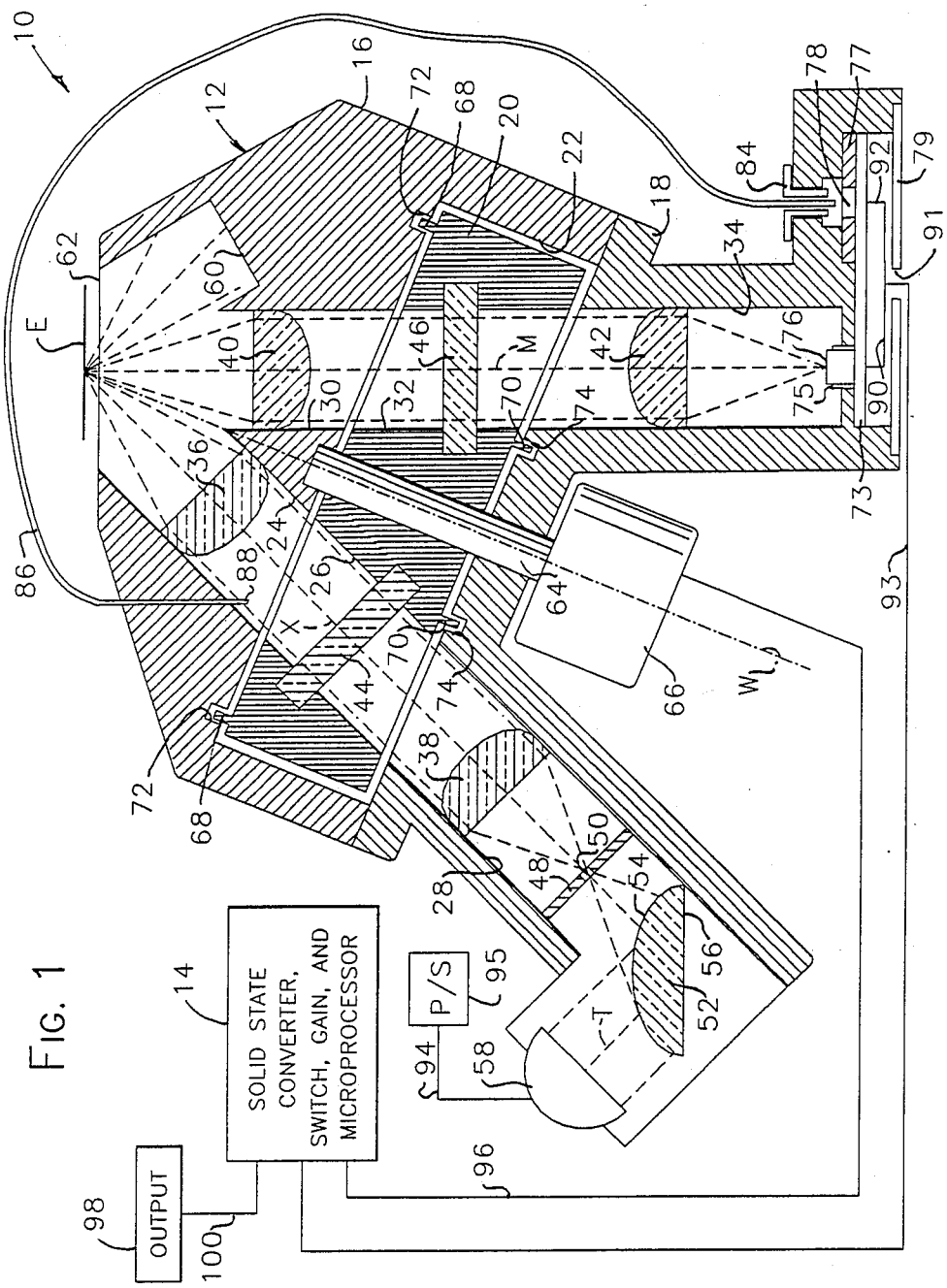
FIG. 1 is a fragmentary cross section illustrating the optical system of the present invention.

In FIG. 1 of the drawings, the optical system of the present invention in generally designated by the reference numeral 10 and shown to include as major components: an optics module or head generally designated by the reference numeral 12 and a solid state processing and control system 14. Optics module 12 reads a biological sample located generally at E, a location light sealed from other components of the instrument which are not shown.

The optics module 12 includes an upper housing section 16 fixedly connected to a lower housing section 18 in a light tight manner. A filter wheel 20 is rotatably supported within a corresponding cylindrical cavity 22 in the upper housing section 16.

With the filter wheel 20 in the position shown in FIG. 1, an excitation optical path having an optical axis (X) is defined by a first rectangular opening 24 in the upper housing section 16, a second rectangular opening 26 in the filter wheel 20, and a third rectangular opening 28 in the lower housing section 18. Each of the openings 24, 26, and 28 have substantially the same dimensions and are coaxial with the excitation optical axis (X). Similarly, an emission optical path having an optical axis (M) is made up of a first rectangular opening 30 in the upper housing section 16, a second rectangular opening 32 in the filter wheel 20, and a third rectangular opening 34 in the lower housing section 18. Each of the rectangular openings 30, 32, and 34 have substantially the same dimensions and are coaxial along the emission optical axis (M).

Aspheric optical lenses 36, 38, 40, and 42 are mounted within and normal to the longitudinal axis of each of the rectangular openings 24, 28, 30, and 34, respectively. A first matched pair of excitation and emission bandpass filters 44 and 46 are supported in the cylindrical openings 26 and 32 of the filter wheel 20 normal to the excitation and emission optical axis (X) and (M), respectively. A rectangular opaque element 48 having a small sized rectangular aperture 50 at its center is mounted within the rectangular opening 28 transverse to the excitation optical axis (X).

Adjacent the lower end of the rectangular opening 28 in the lower housing section 18 is a reflecting and focusing element 52 having a convex refracting front surface 54 and a mirrored plano rear surface 56. The element 52 is positioned at an angle of 45° with respect to the excitation optical axis (X). The lower housing section 18 supports a replaceable tungsten halogen bulb and integral reflector unit 58 so as to provide radiant energy along an optical axis (T) at a right angle with respect to the excitation optical axis (X) and at 45° with respect to the planar rear surface 56 of the focusing and reflecting element 52.

The upper housing section 16 includes a light trap 60 adjacent the rectangular opening 30 and opposite the rectangular opening 24. The openings 24 and 30 and the light trap 660 intersect at their upper ends and form a large opening or read port 62 in the top surface of the upper housing section 16.

The filter wheel 20 is mounted on a shaft 64 for rotation about an axis (W) which bisects the 45° angle (A) (FIG. 3) between the excitation path optical axis (X) and the emission optical axis (M). The shaft 64 is journaled for rotation in the upper and lower housing sections 16 and 18 in a conventional manner and is rotatably driven by a bi-directional stepper motor 66.

The filter wheel 20 further includes upper and lower cylindrical flanges 68 (FIGS. 1 and 2) and 70 (FIGS. 1, 4, and 5) which are received by corresponding cylindrical recesses 72 and 74 in the upper and lower housing sections 16 and 18, respectively. The cylindrical flanges 68, 70 and recesses 72, 74 form a light baffling arrangement or labyrinth which optically separates the excitation and emission optical paths and keeps unfiltered illumination from leaking around the filter wheel 20.

The optical system 10 further includes a main photodetector 76 and a reference photodetector 78, each being a conventional photodetector such as a silicon photodiode. Both photodetectors are mounted on a common circuit board 73 which sits in cavity formed in the housing section 18 at the end of the emission branch of the read head. Photodetector 76 is light sealed from the emission branch by a light seal 75. Reference photodetector 78 receives light from a remote section of the excitation branch via a fiber optic 86 which is coupled to housing 18 via a coupling 84. A light seal 77 prevents any stray light from fiber optic 86 from entering the main photodetector 76.

Outputs from photodetectors 76 and 78 are feed to control system 14 via lines 90 and 92, respectively, which, for convenience, are combined as a single line 93 that passes through a single hole 91 in a cover plate 79 placed over the cavity in which the board 73 sits. In this manner, both photodetectors are isolated from stray light signals and experience more or less the same environment. In addition, cover plate 79 preferably forms part of a metallic enclosure for the photodetectors to isolate them from electromagnetic interference.

The solid state control and processing circuitry 14 (a preferred embodiment of which is shown in detail in FIG. 6) receives the output signals of photodetectors 76 and 78 along lines 90 and 92, respectively. The solid state circuitry 14 provides control signals to the stepper motor 66 along line 96 while light source 58 is connected to a power supply 95 via line 94. An output device 98 such as an optical display or printer outputs concentration levels from the solid state circuitry 14 along a line 100.

Figure 2:
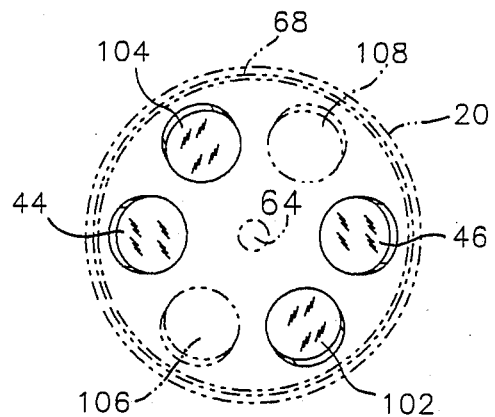
FIG. 2 is a reduced bottom view representing the filter wheel of the present optical system.

As shown in FIG. 2 of the drawings, the filter wheel 20 (shown in phantom lines) includes not only the matched pair of excitation and emission bandpass filters 44 and 46 (FIG. 1), but also a second matched pair of bandpass filters 102 and 104 and a pair of diametrically opposed opaque regions or inserts 106 and 108. The bandpass filters 44, 46, 102, and 104 are shown in solid lines while the remaining portions of the filter wheel are shown in phantom lines to make it clear that each of the bandpass filters slants downwardly from the exterior circumference of the wheel toward the base of the shaft 64. Although the filter wheel 20 itself is of a generally cylindrical design, each of the bandpass filters 44, 46, 102, and 104 rotates about the axis (W) in a substantially inverted conical path. In accordance with the preferred embodiment shown in FIGS. 1 and 3 where the excitation optical path and emission optical path intersect at an acute angle (A) of 45°, more or less. The apex angle of the inverted cone corresponding to the surface defined by each of the bandpass filters is 135°, more or less. As such, the planar upper and lower surfaces of each bandpass filter are oriented normal to the collimated light in each of the excitation and emission optical paths or branches. Since the filtering properties of each of the bandpass filters 44, 46, 102, and 104 vary with respect to the incidence angle of the illumination to be filtered, shifts in the central wavelength are minimized by having the filters oriented normal to the optical path and located within a section of the optical branch where the light is collimated.

Figure 7:
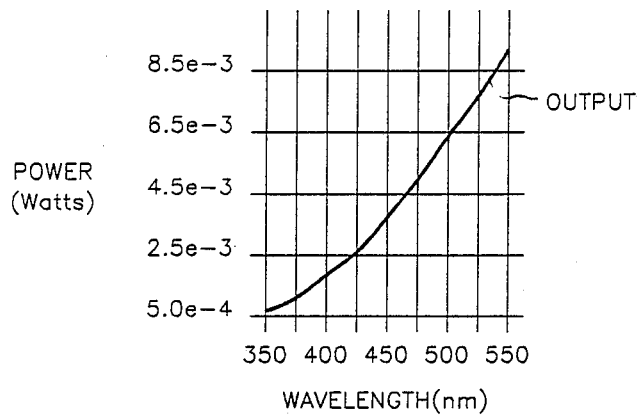
FIG. 7 is a schematic chart representing the spectral output of a conventional tungsten halogen source.

In accordance with the preferred embodiment, each of the bandpass filters 44 and 46 are made entirely of Schott absorbing glass with the excitation filter 44 passing light of a narrow bandwidth around 360 nm, and the emission filter 46, which has a neutral density evaporative coating, passing light of a narrow bandwidth about 450 nm. In accordance with the same embodiment, the excitation and emission bandpass filters 102 and 104 are constructed in a conventional manner as filter packs of absorbing glasses and six cavities of evaporative optical bandpass filters with the absorbing glass being used primarily as a highpass filter while the bandpass cavities are used for the specific bandpass and sharp cutoffs. The excitation filter 102 is designed to transmit light in a narrow bandwidth between 545 and 555 nm, while the emission bandpass filter 104 transmits light having wavelengths in the narrow bandwidth from about 575 to 585 nm. It is preferred that the diametrically opposed opaque regions 106 and 108 are defined simply by opaque sections of the filter wheel 20 between the filters 44 and 102 and 46 and 104, respectively. However, it is contemplated that the opaque surfaces 106 and 108 can be opaque inserts placed within cylindrical openings in the filter wheel 20 in much the same way as the bandpass filters. In accordance with the same preferred embodiment, the tungsten halogen bulb and reflector unit 58 is a 35 watt tungsten halogen bulb and integral reflector which is commercially available at low cost. The integral reflector operates in a conventional manner to reverse the direction of rearwardly traveling radiation from the bulb filament, form a substantially collimated beam which merges with the direct radiation from the bulb filament, thereby making the most efficient use of the output of the lamp, and is IR transmissive to remove heat from the system. As shown in FIG. 7 of the drawings, such a tungsten halogen bulb provides both ultraviolet and visible radiation output. The power output spectrum of the lamp can be calculated for purposes of estimating and optimizing optical power using Planck's blackbody formula.

Figure 3:
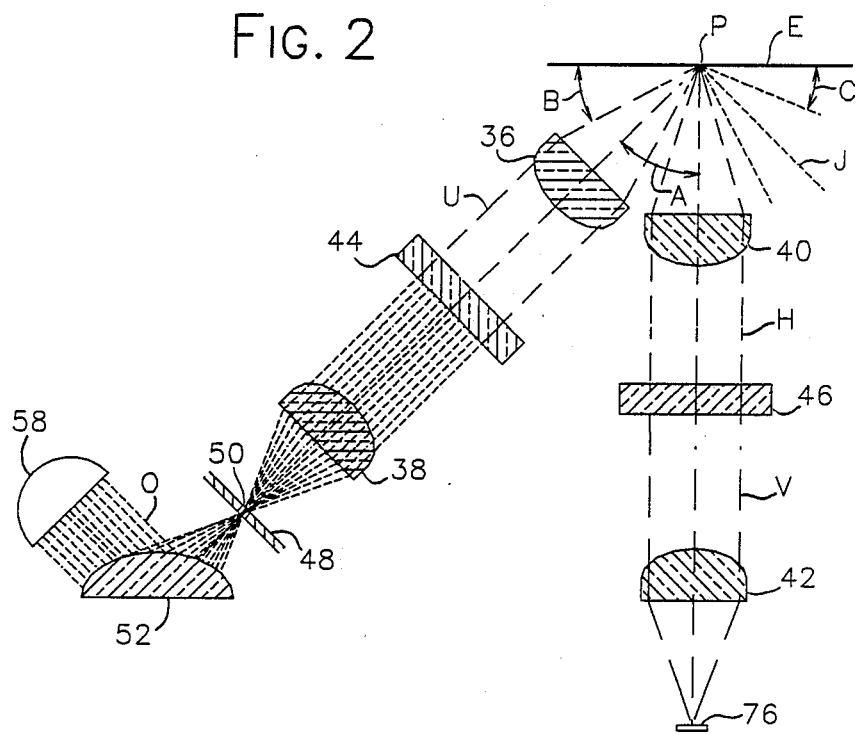
FIG. 3 is a schematic cross section illustrating the radiant energy throughput of the present optical system.

With reference to FIG. 3 of the drawings, combined ultraviolet and visible radiation output O from the lamp and reflector combination 58 is folded and simultaneously focused onto the aperture 50 by the reflecting and refracting element 52. The illuminated aperture 50, forming an object for analytical purposes, is imaged by the pair of aspheric lenses 38 and 36 onto a plane coincident with the signal layer of an assay element or sample (E). The aspheric lens 38 collects and collimates the ultraviolet and visible radiation which passes through the aperture 50 so that it is directed normal to the lower planar surface of the bandpass filter 44. As such, the filtering capabilities of the excitation bandpass filter 44 are maximized. The filter 44 blocks the passage of substantially all radiation having a wavelength of 390 nm or greater and allows the passage of radiation (U) of a narrow bandwidth about 360 nm with a peak transmittance at approximately 370 nm. The aspheric lens 36 collects the radiation (U) and converges it at a point (P) coincident with the signal layer of the assay element (E). The focused excitation radiation (P) produces specular reflection (J) and diffuse reflection and fluorescence (H).

In order to optimize specular light control and to reduce space requirements, the aspheric lenses 36, 38, 40, and 42 are shaved or trimmed to be rectangular in shape so that the excitation light aimed at the assay element (E) does not come in at too small of a raking angle (B) with the lowest projected ray being at about 37° with respect to the assay element plane and the angle (C) of the lowest ray of specularly reflected light being about 33°. In an effort to detect the diffuse fluorescence given off by the assay element (E) and to minimize spurious specular reflection signals, the excitation optical path is directed at 45° with respect to the plane of the assay element (E) while the emission or detection optical path lies normal to the plane of the assay element and the light trap 60 is positioned to catch and absorb the specularly reflected radiation (J). Additionally, the interior surfaces of the housing sections 16 and 18 and all of the surfaces of the filter wheel 20 (excluding the bandpass filters) are anodized, painted or colored flat black so as to eliminate spurious light.

The aspheric lens 40 collects and collimates the diffuse reflection and fluorescence (H) from the assay element (E). The collection lens 40 is trimmed such that the entire lens misses the specular reflections (J) off the surface of the sample element.

The emission filter 46 transmits diffuse fluorescence (V) while rejecting or blocking any diffusely reflecting excitation wavelengths and any specular component (J) which may find its way into the collection path. In accordance with the preferred embodiment wherein the emission bandpass filter 46 is made entirely of Schott absorbing glass, the filter 46 blocks all wavelengths of less than 425 nm and passes a narrow bandwidth of light having a wavelength about 450 nm with a peak transmittance at about 470 nm. The excitation and emission bandpass filters 44 and 46 are chosen to have bandpass and absorption or "blocking" properties for proper isolation between excitation and emission wavelengths. Measured quantitatively, the "blocking" factor or the ratio of incident white light to transmitted light of the filters 44 and 46 is $10^{-8}$.

The diffuse fluorescence (V) transmitted by the bandpass filter 46 is collected and focused on the photodetector 76 by the aspheric lens 42. To maximize the signal at the wavelengths of interest, that is in the ultraviolet region of the spectrum, all of the aspheric lenses 36, 38, 40, and 42 are made of an optical material, such as optical plastic, which is highly transmissive at the wavelengths of interest. For example, commercially available lenses formed of Rohm and Haas UVT 100 Acrylic provide the desired transmittance. For cost purposes, each of these lenses are of identical construction and of conventional design.

To normalize readings to account for changes in both the output wavelength or intensity of the tungsten bulb 58, optical fiber pickoff 88 is placed downstream of the excitation filter 44 to provide a portion of the filtered excitation light to the reference photodetector 78. As such, the output signal of the reference detector 78 corresponds to the characteristics of the excitation light and is used in the signal processing algorithm to compensate for variations in bulb output.

Figure 4A:
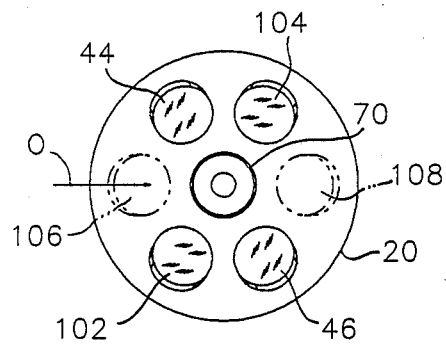
FIGS. 4A-C are reduced top plan views representing the sequential positions of the filter wheel during the use of a first pair of matched bandpass filters.
Figure 5A:
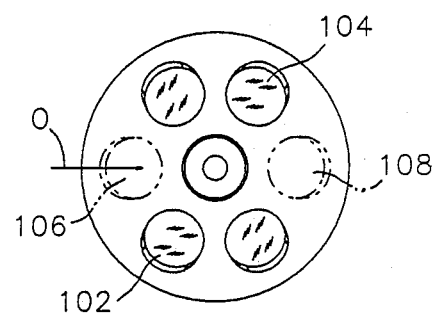
FIGS. 5A-C are reduced top plan views illustrating the sequential positions of the filter wheel during the use of a second matched pair of bandpass filters.
Figure 4B:
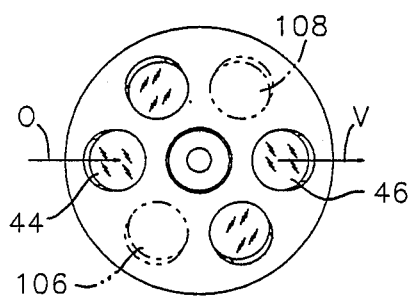
Figure 5B:
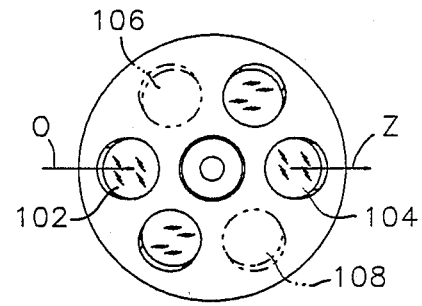
Figure 4C:
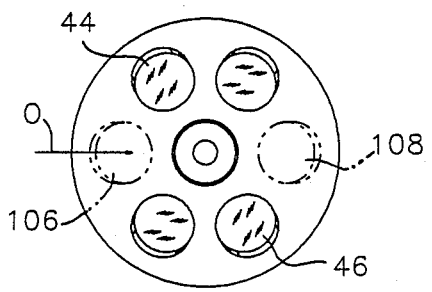
Figure 5C:
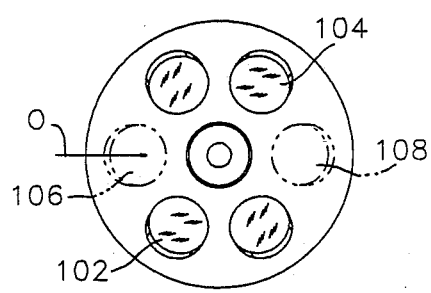

FIGS. 4A–4C depict the three sequential positions of the filter wheel 20 during a fluorescence analysis measurement cycle employing the first matched pair of bandpass filters 44 and 46. FIGS. 5A–5C illustrate the three sequential positions of the filter wheel 20 during analysis utilizing the second matched pair of bandpass filters 102 and 104. The first and third positions of the filter wheel 20 in both of the sequences of FIGS. 4A–4C and FIGS. 5A–5C are the same. In other words, the filter wheel 20 is in the same position at the beginning and end of each of the measurement cycles no matter which matched pair of bandpass filters is being used. As shown in FIGS. 4A, 4C, 5A, and 5C, the filter wheel 20 begins and ends a measurement cycle in a position with the opaque surface 106 blocking the excitation optical path and the opaque surface 108 blocking the emission optical path. To get to the position shown in FIG. 4B, the filter wheel 20 is rotated 60° counterclockwise by the stepper motor 66. In the position shown in FIG. 4B, the excitation bandpass filter 44 is in the excitation optical path and the emission bandpass filter 46 is in the emission optical path (FIGS. 1–3). The filter wheel 20 is brought to the position shown in FIG. 4C from the position shown in FIG. 4B by driving the motor 66 so as to rotate the filter wheel 60° in a clockwise direction. FIGS. 5A and 5C show the filter wheel 20 in the same positions shown in FIGS. 4A and 4C. The filter wheel 20 is brought to the position shown in FIG. 5B by having the stepping motor 66 rotate the filter wheel 60° clockwise. In the position shown in FIG. 5B, the excitation bandpass filter 102 is located in the excitation optical path and the emission bandpass filter 104 is located in the emission optical path. The arrow labeled (O) in each of FIGS. 4A–4C and 5A–5C represents the collimated combination of ultraviolet and visible radiation provided by the collecting and collimating lens 38. The arrow labeled (V) in FIG. 4B represents the emission radiation transmitted through the filter 46 to be collected and focused by the lens 42 onto the main photodetector 76 (FIG. 3). The arrow labeled (Z) represents the radiant energy which is transmitted by the bandpass filter 104 to be collected and focused on the main photodetector 76 by the aspheric lens 42.

Figure 6:
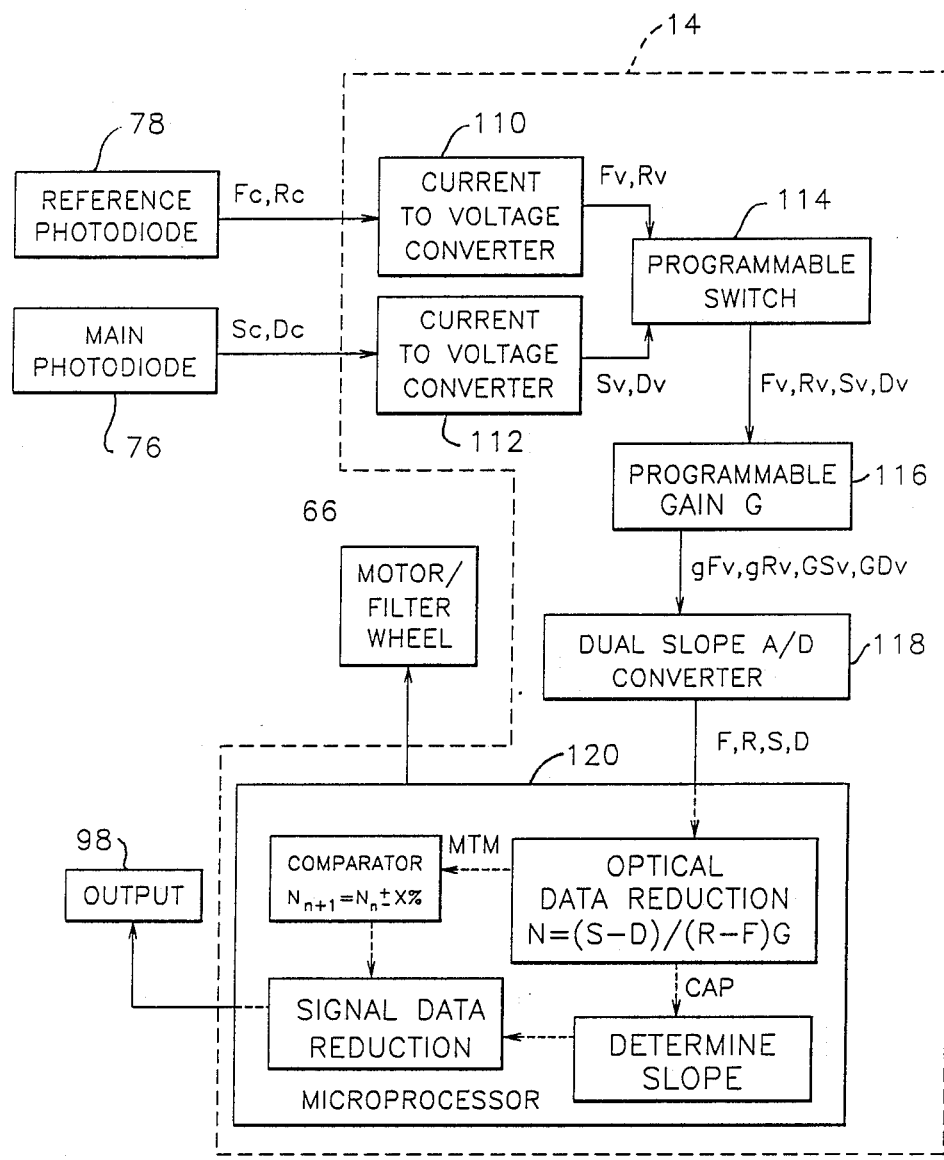
FIG. 6 is a schematic block diagram illustrating the solid state circuitry of the present optical system.

As shown in FIG. 6 of the drawings, the solid state control and processing circuitry 14 of FIG. 1 includes a pair of current-to-voltage converters 110 and 112, a programmable switch 114, a programmable gain 116, a dual slope analog-to-digital converter 118, and a microprocessor 120. Generally, in the process for fluorescent spectroscopy in accordance with the present invention, current signals $S_c, D_c$ (main channel signals), and $F_c, R_c$ (reference channel signals) from each of the photodetectors 76 and 78, respectively, are amplified and converted to voltage signals $S_v$, $D_v$, $F_v$, $R_v$ by passing through the converters, for example, transimpedance amplifiers, 110 and 112. The programmable switch 114 provides one of the voltage signals $S_v$, $D_v$, $F_v$, $R_v$ at a time to the programmable gain amplifier 116 having an amplification which is selectable in factors of 2 over a range from 1x to 128x to produce gain outputs $gF_v$, $gR_v$, $GS_v$, $GD_v$. The gain for each photodiode, (G) for the main photodiode 76 an (g) for the reference photodiode 78, is selected separately. Each of the outputs $gF_v$, $gR_v$, $GS_v$, $GD_v$, from the programmable gain 116 is fed sequentially to the dual slope A/D converter 118 and converted to respective digital signals (F), (R), (S), (D). The dual slope converter 118 includes, for example, a capacitor which is charged by a signal for 700 ms. After this period, the capacitor is discharged to a specific value. The time required for this discharge is precisely counted The value of this precise count represents a digital value corresponding to the analog input signal. The digital values (F), (R), (S), (D) are transmitted one at a time to the microprocessor 120 for data reduction.

More particularly and with reference again to FIGS. 4A–4C of the drawings, a fluorescence measurement cycle employing the pair of bandpass filters 44 and 46 begins with the filter wheel in the position shown in FIG. 4A. In this position the opaque region 106 blocks the transmission of excitation illumination so that the current signal F developed by the reference channel 78 is indicative of reference channel photodetector and amplifier dark signals. Next, the stepper motor 66 is driven by the microprocessor 120 so that the filter wheel 20 assumes the position shown in FIG. 4B. In this position, the excitation and emission bandpass filters 44 and 46 are located in the excitation and emission optical paths. As such, the reference photodetector 78 provides the current signal $R_c$ corresponding to the reference channel excitation signal plus dark signal, and the main photodetector 76 provides the current signal $S_c$ representing the main channel emission signal plus dark signal. Next, the microprocessor 120 drives the stepper motor 66 so as to rotate the filter wheel 20 to the position shown in FIG. 4C. In this position, the opaque region 108 blocks the transmission of illumination along the emission optical path so that the current output $D_c$ of the main photodetector 76 corresponds to a main channel dark signal. This cycle is repeated for each measurement point associated with the bandpass filters 44 and 46. A similar cycle providing for the development of the four photodiode current signals $F_c$, $R_c$, $S_c$, and $D_c$ but employing the filter wheel positions shown in FIGS. 5A–5C is preformed for each measurement point employing the bandpass filter pair 102 and 104. The start of each measurement cycle during which a single signal is converted occurs within 250 ms of the last cycle to minimize the effects of noise and long term drift.

In the microprocessor 120 data reduction provides a fluorescence measurement number $N = (S-D)/(R-F)G$ where (S) is the main channel emission signal, (D) is the main channel dark signal, (R) is the reference or fiber channel excitation signal, (F) is the reference or fiber channel dark signal, and (G) is the gain of the of the main detector channel.

The optical system 10 of the present invention is particularly suited for use as a fluorometer in an immunoassay instrument for determining antigen or antibody concentrations using either multilayer (MTM) or capillary (CAP) type assay elements. Capillary type assay elements provide a diffusely fluorescent signal which differs in wavelength from the excitation wavelength by about 90 nm. In response to excitation radiation, each of the multilayer and capillary type assay elements behaves like a Lambertian source and provides a diffuse fluorescence signal whose compliance with the Lambertian rules depends on the character of the assay element being measured.

When analyzing a multilayer competitive type assay element in which the conjugate, the fluorescently labeled antibody, antigen, etc., is excited and emits an output signal that varies in inverse relation to the concentration of the analyte present, the multilayer assay element is subjected to an initial fluorescence measurement cycle utilizing the opaque surfaces 106 and 108 and the matched pair of bandpass filters 102 and 104 (FIGS. 5A-5C) before the fluid sample is added to the assay element so as to produce a dry fluorescence measurement. Then, the fluid sample is added to the multi-layer assay element, and this wet assay element is read using the same fluorescence measurement cycle (FIGS. 5A-5C). The wet measurement is divided by the initial dry measurement to produce a normalized multi-layer assay element measurement which is fitted to a calibration curve to find the corresponding analyte concentration. Thus, when analyzing a multilayer assay element (MTM) there is no signal differentiation. Any background fluorescence produced by the fluid sample itself is so insignificant in comparison to the main fluorescent signal given off by the fluorophore adjacent the front surface of the assay element that the background fluorescence can be ignored. For example, the fluorescence signal produced by a blood serum sample at the wavelength at which the element is being read is very low and the volume of blood serum at the reading layer of the assay element is so small that any background fluorescence contribution of the blood serum can be neglected.

When analyzing a capillary type assay element (CAP) in which the amount of enzyme is measured to determine the concentration of species under assay, a new fluorophore, such as rhodomine which does not effect fluorescence measurements taken using the bandpass filters 44 and 46 (FIGS. 4A-4C), is added to the assay element. It is preferred to add this new fluorophore to the assay element substrate. However, it is contemplated that this new fluorophore can be added to the fluid sample. Fluorescence measurements are delayed a predetermined time, for example 2½ minutes, after which it is known that the fluorescence measurements are changing at a fixed linear rate. Following this delay, multiple measurements are taken at fixed intervals, such as one minute intervals, using the opaque regions 106 and 108 and the bandpass filters 44 and 46 (FIGS. 4A-4C) and the slope of these measurement is determined. Next, a new fluorophore fluorescence measurement is taken using the opaque surfaces 106 and 108 and the bandpass filters 102 and 104 (FIGS. 5A-5C) and the slope of the initial four measurements is divided by this new fluorophore measurement to produce a normalized slope value. This normalized slope value is related to the concentration of the analyte under study through a predetermined calibration curve. Background fluorescence signals produced by the fluid sample itself are insignificant.

In addition to the above measurements, rate studies using, for example, MTM or CAP assays are done by taking a series of readings at predetermined or, at least, determinable spaced intervals.

Although it is not shown in the drawings, it is to be understood that the microprocessor 120 monitors the filter wheel position by monitoring the output signals of the reference photodetector 78 and keeping track of the rotations of the stepper motor 66. Further, it is contemplated that the microprocessor 120 may receive additional input such as type of assay element, filter wheel position, etc. from conventional sensor elements such as additional photointerruptors, proximity switches, or digital input provided by a system user via a keyboard, numeric keypad, or touch screen. Such input devices may form part of the optical system, fluorometer, or analytical instrument.

Given the following equation:

$$P(s) = P(a) \times T(l)^2 \times T(f) \times \Omega/(4\pi)$$

where P(s) is the power on the slide or assay element,
P(a) is the power out of the lamp in the actinic region (53 mW MTM, 14 mW CAP),
T(l) is the transmission of the aspheric lenses (0.90),
T(f) is the transmission of the excitation filter (0.50 MTM, 0.30 CAP), and
$\Omega$ is the collection solid angle of the lens (0.3).

An example optical system in accordance with the present invention provides a P(s)~550 μWatts for an MTM assay and a P(s)~81 μWatts for a CAP assay.

Also given that the minimum output of an MTM assay element is P(e)~P(s)×1E-6 and for a CAP assay element is P(e)~P(s)×1E-4
where P(e) is the emission signal. Then, the power on the main photodetector of the same example optical system is:

$$P(d) = P(e) \times T(l)^2 \times T(f2) \times \Omega/(4\pi)$$

Where P(d) is the power on the detector,
T(f2) is the transmission of the emission filter (0.50 MTM, 0.08 CAP).

Using the above equation, the minimum power on the main photodetector developed by an MTM assay is P(d) ~5E-12W (5 picowatts) and by a CAP assay is P(d)~7E-11W (70 picowatts).

With the above values, the theoretical performance for the present detector circuitry at 5 picowatts of signal yields ~400/1 Signal to Noise Ratio (S/N), and at 70 picowatts of signal yields ~5000/1 S/N.

Figure 8:
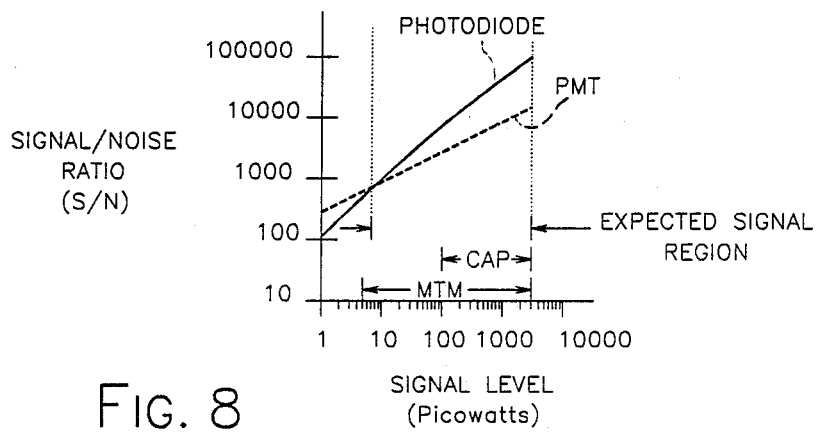
FIG. 8 is a schematic chart comparing the signal to noise ratios of a photomultiplier tube and a photodiode/amplifier combination.

As shown in FIG. 8 of the drawings and assuming the same timing parameters, the signal to noise ratio of a conventional silicon photodiode, such as the main photodetector 76 of the present invention, is equal to or greater than the signal to noise ratio of a conventional photomultiplier tube (PMT) in a signal region of about 7 to 3,000 picowatts. Even though conventional wisdom in the fluorometer art has been to use a photomultiplier tube for sensing low levels of sample emitted fluorescence encountered when using a low ultraviolet light producing source, the optical system of the present invention beneficially employs a tungsten halogen bulb and solid state detectors. This is made possible because the present optical system provides an emission light signal of from about 7 to 3000 picowatts. This relatively high level emission light signal corresponds to a more than adequate signal to noise ratio for the photodiode 76. As such, the use of solid state photodetectors and a low cost low ultraviolet output light source in the optical system of the present invention provides for a low cost optical system without compromising the reliability of the test results.

The expected signal region associated with the use of a multilayer assay element ranges from about 4 to 3000 picowatts. The expected signal region using a capillary type assay element ranges from about 100 to 3000 picowatts. The difference in MTM and CAP signal regions is due in part because the fluorescence in the multilayer element is due to the presence or absence of tagged antigens or antibodies, while the fluorescence in a capillary element comes from an enzyme amplification.

Thus, it will be appreciated that as a result of the present invention, a highly effective optical system for use in a fluorometer is provided and by which the stated objectives, among others, are completely fulfilled. It is contemplated that modifications and/or changes may be made in the illustrated embodiment without departure from the invention. For example, while a filter wheel having two matched pairs of bandpass filters is demonstrated in the illustrated embodiment, a filter wheel having a greater or lesser number of pairs of bandpass filters may be used.

Further, it will be apparent to those skilled in the art from the foregoing description and accompanying drawings that additional modifications and/or changes may be made, again without departure from the invention. Accordingly, it is expressly intended that the foregoing description and accompanying drawings are illustrative of a preferred embodiment only, not limiting, and that the true spirit and scope of the present invention be determined by reference to the appended claims.

What is claimed is:

1. An optical system for use in analyzing the concentration of a constituent in a fluid sample or the like by irradiating the sample with excitation energy within a first band of wavelengths, determining the amount of radiant energy emitted by the sample within a second band of wavelengths, and relating the amount of emitted radiation to the concentration of the constituent under investigation, said optical system comprising:
   a radiation source for providing light to excite the sample;
   excitation and emission optical branches at least one of which includes optical means highly transmissive at the wavelengths corresponding to the light emitted by said radiation source;
   solid state photodetector means for receiving radiation along said emission branch and providing an output indicative of the sample emitted radiation;
   means positioned along said excitation branch for selectively filtering said radiation source to provide said excitation energy within the first band of wavelengths and means positioned along said emission optical branch for filtering radiation from the sample such that the spectral response of said photodetector means is limited to wavelengths within the second band of wavelengths, said filter means including at least one matched pair of excitation and emission bandpass filters and means for blocking the passage of light along each of said optical branches, said filter means for selectively filtering or blocking having at least first and second working positions, each of said excitation and emission filters off said at least one matched pair being located in the excitation and emissions branches, respectively, in said first position, and each of the excitation and emission branches being blocked by said blocking means in said second position.

2. The optical system of claim 1 wherein said solid state photodetector means further includes a reference photodetector for receiving and providing an output signal indicative of the excitation illumination provided by said radiation source when said bandpass filters are in said first position and for providing a dark signal output when said blocking means are in said second position.

3. The optical system of claim 2 wherein said solid state photodetector means includes a main photodetector along said emission branch and each of said main and reference photodetectors are photodiodes which provide output in the form of current signals.

4. The optical system of claim 3 wherein said solid state photodetector means further includes transimpedance amplifiers, one per photodetector, for converting and amplifying the current output signals of each photodetector to a voltage signal.

5. An optical system for use in a fluorometric device adapted to analyze the concentration of a constituent in a fluid sample or the like by irradiating the sample with excitation energy within a first band of short wavelengths, determining the amount of fluorescent radiant energy emitted by the sample within a second band of longer wavelengths, and relating the amount of emitted fluorescent radiation to the concentration of the constituent under investigation, said optical system comprising:
   a radiation source low in ultraviolet content for providing light to excite the sample;
   excitation and emission optical branches each including optical means highly transmissive in the ultraviolet region of the spectrum;
   solid state photodetector means for receiving radiation along said emission branch and providing an output indicative of the sample emitted fluorescence;
   means positioned along said excitation branch for selectively filtering said radiation source to provide said excitation energy within the first band of short wavelengths and means positioned along said emission optical branch for filtering radiation rom the sample such that the spectral response of said photodetector means is limited to wavelengths within the second band of longer wavelengths, said filter means including at least one matched pair of excitation and emission bandpass filters and means for blocking the passage of light along each of said optical branches, said filter means for selectively filtering or blocking having at least first and second working positions, each of said excitation and emission filters of said at least one matched pair being located in the excitation and emissions branches, respectively, in said first position, and each of the excitation and emission branches being blocked by said blocking means in said second position.

6. The optical system of claim 5 wherein said solid state photodetector means further includes a reference photodetector for receiving and providing an output signal indicative of the excitation illumination provided by said radiation source when said bandpass filters are in said first position and for providing a dark signal output when said blocking means are in said second position.

7. The optical system of claim 6 wherein said fluorometric device operates as a dual channel fluorometer and said at least one matched pair of excitation and emission bandpass filters comprise two matched pairs of excitation and emission bandpass filters thereby providing for a third operating position in which the other of the matched pairs is placed in the excitation and emission branches.

8. The optical system of claim 7 wherein said photodetector means includes a main photodetector along said emission branch and each of said main and reference photodetectors are photodiodes which provide output in the form of current signals.

9. The optical system of claim 8 wherein said solid state photodetector means further includes transimpedance amplifiers, one per photodetector, for converting and amplifying the current output signals of each photodetector to a voltage signal.

10. The optical system of claim 8 wherein said solid state photodetector means further includes a programmable switch for receiving and selectively transmitting the voltage signal output of said transimpedance amplifiers to a programmable gain amplifier having an amplification selectable in factors of two over a range from 1 x to 128 x and providing for the separate selection of gain for each of the outputs of each transimpedance amplifier.

11. The optical system of claim 10 wherein said solid state photodetector means further includes a dual-slope A/D converter and a processor for data reduction, said dual-slope A/D converter operating to receive the output of said programmable gain amplifier and provide a digital count value representative thereof and to transmit this count value to said processor for data reduction.

12. The optical system of claim 11 wherein said processor provides a fluorescence measurement based on a reference photodetector dark signal (F), a reference photodetector excitation signal (R), a main photodetector emission signal (S), and a main photodetector dark signal (D) using the algorithm $N=(S-D)/(R-F)G$ where (G) is the gain of the main photodetector signal.

13. The optical system of claim 12 wherein said fluorometric device comprises an immunoassay instrument capable of performing immunoassays of blood serum and other biological fluid samples by front-surface fluorescence spectroscopy of one or more assay elements, said instrument including means for supporting an assay element above said optical system in position to be analyzed.

14. A method for fluorescence spectroscopic analysis of a biological fluid sample using an optical system having a source of illumination, excitation and emission optical branches, a reference photodetector for receiving filtered excitation radiation, a main photodetector for receiving filtered sample emitted fluorescence, and means for selectively filtering or blocking said excitation and emission optical branches, comprising the steps of:

developing a reference photodetector dark signal (F),
developing a reference photodetector excitation signal (R),
developing a main photodetector emission signal (S),
developing a main photodetector dark signal (D), and
processing said signals to produce a fluorescence measurement (N) where:

$$N=(S-D)/(R-F)G$$

and where (G) is the gain of the main photodetector signals.

15. An optical system for use in a fluorometric device adapted to analyze the concentration of a constituent in a fluid sample or the like by irradiating the sample with excitation energy within a first band of short wavelengths, determining the amount of fluorescent radiant energy emitted by the sample within a second band of longer wavelengths, and relating the amount of emitted fluorescent radiation to the concentration of the constituent under investigation, said optical system comprising:

a tungsten halogen source low in ultraviolet content for providing light to excite the sample;
excitation and emission optical branches each including optical means highly transmissive in the ultraviolet region of the spectrum;
a solid state photodiode for receiving radiation along said emission branch and providing an output indicative of the sample emitted fluorescence; means positioned along said excitation branch for selectively filtering said radiation source to provide said excitation energy within the first band of short wavelengths and means positioned along said emission optical branch for filtering radiation from the sample such that the spectral response of said photodetector means is limited to wavelengths within the second band of longer wavelengths.

* * * * *